US010090116B2

(12) United States Patent
Curchoe et al.

(10) Patent No.: US 10,090,116 B2
(45) Date of Patent: Oct. 2, 2018

(54) BIOLOGICAL SUPERCAPACITOR STRUCTURE AND METHOD FOR MANUFACTURING AND USE OF THE SAME

(71) Applicant: 32ATPs, LLC, San Diego, CA (US)

(72) Inventors: Carol Lynn Curchoe, San Diego, CA (US); Shelley Minteer, Salt Lake City, UT (US)

(*) Notice: Subject to any disclaimer, the term of this patent is extended or adjusted under 35 U.S.C. 154(b) by 206 days.

(21) Appl. No.: 14/941,221

(22) Filed: Nov. 13, 2015

(65) Prior Publication Data

US 2016/0145669 A1    May 26, 2016

Related U.S. Application Data

(60) Provisional application No. 62/080,117, filed on Nov. 14, 2014.

(51) Int. Cl.
| | | |
|---|---|---|
| C12Q 1/00 | (2006.01) | |
| H01G 11/38 | (2013.01) | |
| H01G 11/36 | (2013.01) | |
| H01G 11/28 | (2013.01) | |
| H01G 11/62 | (2013.01) | |
| H01G 11/52 | (2013.01) | |
| H01G 11/04 | (2013.01) | |
| H01G 11/68 | (2013.01) | |

(52) U.S. Cl.
CPC .............. *H01G 11/62* (2013.01); *C12Q 1/001* (2013.01); *C12Q 1/004* (2013.01); *H01G 11/04* (2013.01); *H01G 11/28* (2013.01); *H01G 11/38* (2013.01); *H01G 11/52* (2013.01); *H01G 11/36* (2013.01); *H01G 11/68* (2013.01); *Y02E 60/13* (2013.01)

(58) Field of Classification Search
CPC ........ C12Q 1/002; C12Q 1/004; H01G 11/32; H01G 11/36; H01G 11/68; H01G 11/52; H01G 11/28
USPC .......................... 361/502, 508, 516; 429/523
See application file for complete search history.

(56) References Cited

U.S. PATENT DOCUMENTS

2011/0039164 A1*  2/2011  Akers ..................... H01M 4/86
                                                        429/401

FOREIGN PATENT DOCUMENTS

WO    WO 2014135787 A1 *  9/2014  ............. H01G 11/36

OTHER PUBLICATIONS

Pankratov, D., Blum, Z., Suyatin, D. B., Popov, V. O. and Shleev, S. (2014), Self-Charging Electrochemical Biocapacitor. Chemelectrochem, 1: 343-346. doi: 10.1002/celc.201300142.

* cited by examiner

*Primary Examiner* — Eric Thomas
*Assistant Examiner* — Arun Ramaswamy

(57) ABSTRACT

A biological supercapacitor comprising at least one pair of electrodes that comprise immobilized biological materials that includes enzymes. The enzymes are immobilized to the electrodes and may be isolated enzymes, enzyme cascades comprising multiple enzymes, whole cells, organelles from cells, or parts of organelles from cells. An aspect of the disclosed biological supercapacitor is that a byproduct is water. The disclosed biological supercapacitor combines the energy density of a battery with the power density of a supercapacitor in order to reduce the size and weight of the energy storage devices. Methods of fabrication and of use of the biological supercapacitor are also disclosed.

1 Claim, 3 Drawing Sheets

BIOLOGICAL SUPERCAPACITOR STRUCTURE AND METHOD FOR MANUFACTURING AND USE OF THE SAME

RELATED APPLICATIONS

This application claims the benefit of U.S. Provisional Application No. 60/097,277, filed Nov. 14, 2014; the disclosures of which is hereby incorporated by reference.

FIELD OF THE INVENTION

The present invention is directed in general to biological based supercapacitors, their methods of manufacture, and methods of use. More specifically, the invention is directed to biological supercapacitors comprising any biological capable of providing transfer of electrons between the fuel fluid and electron conductor and their method of manufacture and use.

BACKGROUND

Mitochondria are the organelles of the living cell that contain several (but not all) of the protein pathways of metabolism, including the citric acid cycle and the electron transport chain. They are responsible for a variety of metabolic processes including fatty acid metabolism and pyruvate oxidation, while pyruvate is produced outside of the mitochondria from glycolytic pathway oxidation of sugars. The citric acid cycle is a key metabolic pathway that unifies carbohydrate, fat, and protein metabolism. The reactions of the cycle are carried out by enzymes that completely oxidize acetate, in the form of acetyl-CoA, into two molecules each of carbon dioxide and water. Through catabolism of sugars, fats, and proteins, a two-carbon organic product acetate in the form of acetyl-CoA is produced which enters the citric acid cycle.

The reactions of the cycle also convert three equivalents of nicotinamide adenine dinucleotide ($NAD^+$) into three equivalents of reduced $NAD^+$ (NADH), one equivalent of flavin adenine dinucleotide (FAD) into one equivalent of $FADH_2$, and one equivalent each of guanosine diphosphate (GDP) and inorganic phosphate ($P_i$) into one equivalent of guanosine triphosphate (GTP).

Biological supercapacitors harness the catalytic activity of living cells, which are able to conduct electrochemical reactions and produce electrical energy. When using biological materials as catalysts at the anode or cathode of a biological supercapacitor, the catalyst needs to be immobilized at the surface of the electrode.

In its most general aspect, a biological supercapacitor consists of paired electrodes and on one side of the interface a layer of electrons forms. On the opposite side of the interface, a layer of positive ions forms. Together, these two layers are the double layer, which store energy.

The voltage across the interface increases with charge accumulation. In connection with the double layer capacitance phenomenon, no charge transfer (Faradaic) process occurs at the electrode/electrolyte interface. During discharge, the charge stored at the interface is released. The charge/discharge rate is generally determined by the nature and type of the material, its thickness, and the electrolyte.

BRIEF SUMMARY OF THE INVENTION

Biocompatible and "micro" energy sources are critical to the development of novel commercial bioelectronics, such as health monitoring devices (rapid analysis of DNA, RNA, metabolites—i.e. biomolecule to biosensors, disease treatment devices, nanoscale delivery vehicles that require biocompatibility to interface with tissues or single cells, and neural and biochemical prosthesis, i.e. artificial sensory organs that require tissue integration or wireless networks), and consumer portable electronics. Conventional battery size and weight are the key technical limitations in the bioelectronics field. Additionally, though many of the current power sources are rechargeable, the recharging process itself involves interaction with an external electrical energy source.

There is a clear need to reduce the Size and Weight of energy storage devices and conserve Power (SWaP). The present disclosure illustrates an apparatus and methods of use thereof to harness the power of biochemical reactions to generate electrochemical potential in a bio(logical) supercapacitor. The biosupercapacitor of the instant disclosure provides the energy density of a battery combined with the power density of a supercapacitor in order to reduce the size and weight of the energy storage devices.

The biological supercapacitor of the instant disclosure comprises at least one pair of electrodes, a bioanode and a biocathode. Each electrode comprises immobilized biological materials that include enzymes. The supercapacitor further comprises a barrier positioned between the bioanode and biocathode, and an ionic conductor that also contains organic fuel(s). The barrier may comprise a separator, which functions as an electronic insulator. The biological electron donor or acceptor of the bioanode is capable of reacting with a fuel fluid to produce an oxidized form of the fuel fluid, and capable of releasing electrons to the electron conductor. The biological electron donor or acceptor of the biocathode is capable of reacting with an oxidant to produce water, and capable of gaining electrons from the electron conductor. The biological electron donor or acceptor immobilization material present on both the bioanode and the biocathode is capable of immobilizing the biological electron donor or acceptor, thereby adhering it to the bioelectrodes, and is permeable to the fuel fluid and/or the oxidant. In various embodiments, the biological electron donor or acceptor immobilization material is further capable of stabilizing the biological agents.

At least one novel feature of the capacitor resides in the enzymatic electrode structure. The electrodes may be manufactured by immobilizing biological enzyme cascades, either isolated or contained in whole cells or parts of cells, with various materials which possess non faradic or faradic charge transfer characteristics to form the electrode pairs.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

Figure 1:
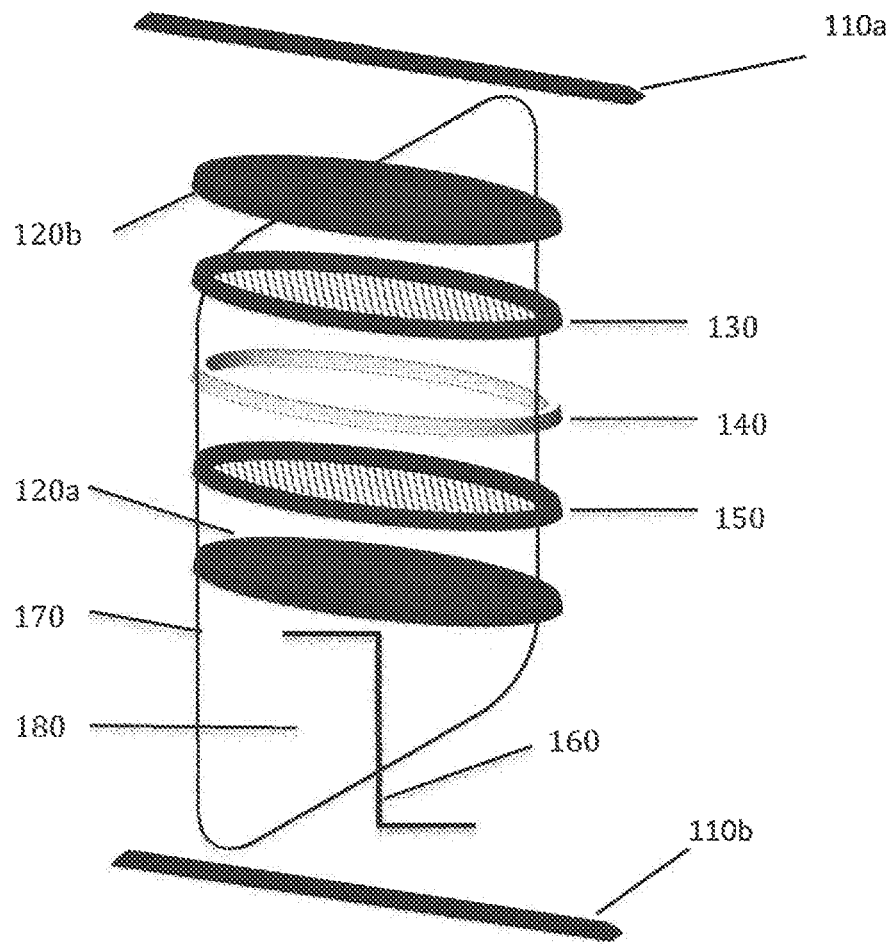
FIG. 1 is a schematic view of a supercapacitor that has biological anode and cathode design.

Mitochondria, enzymes, or enzyme cascades can all be effectively immobilized to create bioelectrodes. Additionally, a means is also provided for electrons to be transferred to and from the electrodes. This can be done either directly from the enzyme to the electrode ("direct electron transfer") or with the aid of other chemicals or substances that transfer electrons from the enzyme to the electrode ("mediated electron transfer"). These chemical substances are termed "electron transfer mediators" or simply "mediators" throughout this disclosure. An advantage of this approach is that biological materials are renewable, non-hazardous, high capacitance, and non-waste generating (complete oxidation of fuels to $CO_2$).

Definitions

The following terms shall have, for the purposes of this application, the respective meaning set forth below.

Electron carrier: An electron carrier is a composition that provides electrons in an enzymatic reaction. Electron carriers include, without limitation, reduced nicotinamide adenine dinucleotide (denoted NADH; oxidized form denoted NAD or NAD+), reduced nicotinamide adenine dinucleotide phosphate (denoted NADPH; oxidized form denoted NADP or NADP+), reduced nicotinamide mononucleotide (NMOSH; oxidized form NMN), reduced flavin adenine dinucleotide (FADH2; oxidized form FAD), reduced flavin mononucleotide (FMNH2; oxidized form FMN), reduced coenzyme A, and the like. Electron carriers include proteins with incorporated electron-donating prosthetic groups, such as coenzyme A, protoporphyrin IX, vitamin B12, and the like. Further electron carriers include glucose (oxidized form: gluconic acid), alcohols (e.g., oxidized form: ethylaldehyde), and the like.

Electron-receiving composition: An electron-receiving composition receives the electrons conveyed to the cathode by the supercapacitor.

Electron transfer mediator: An electron transfer mediator is a composition, which facilitates transfer to an electrode of electrons released from an electron carrier. Redox enzyme: A redox enzyme is an enzyme that catalyzes the transfer of electrons from an electron carrier to another composition, or from another composition to the oxidized form of an electron carrier. Examples of appropriate classes of redox enzymes include: oxidases, dehydrogenases, reductases and oxidoreductases. Additionally, other enzymes, with redox catalysis as their secondary property could be used e.g., superoxide dismutase.

Composition: Composition refers to a molecule, compound, charged species, salt, polymer, or other combination or mixture of chemical entities.

Metabolon: A metabolon is a supramolecular organization of the Krebs cycle enzymes in mitochondria where the continuous surface pattern electrostatically favors efficient intermediate transport between active sites in the complex, known as substrate channeling.

Enzyme cascade: An enzyme cascade is a group of sequential enzymes of metabolic pathways.

Electrocyte: As used herein, an electrocyte is an electrogenic cell.

DETAILED DESCRIPTION OF THE INVENTION

A biological supercapacitor according to the present disclosure includes at least several practical advantages over those known in the art. It has an increased device energy density when compared with carbon capacitors and low-cost biocatalysts instead of costly or rare metals. Moreover, the biological supercapacitors of the instant disclosure are disposable and biodegradable devices.

The current invention achieves high energy storage capability using biologically derived or biomimetic components. The citric acid cycle enzymes, which for purposes of this application are known to occur in a specific enzymatic sequence in the mitochondria, may be used individually or in any combination thereof. They may be crosslinked and removed from the organelle prior to immobilization at the anode or cathode, hereinafter referred to as "bioanode" and "biocathode" respectively.

Enzymes that catalyze oxidation reactions include pyruvate dehydrogenase, isocitrate dehydrogenase, ketoglutarate dehydrogenase, succinate dehydrogenase, and malate dehydrogenase. The other enzymes catalyze additional necessary chemical reactions to rearrange the reactant molecules for the next step of oxidation.

Reference will now be made in detail to the present embodiments of the invention, examples of which are illustrated in the accompanying drawings. Wherever possible, the same reference numbers are used in the drawings and the description to refer to the same or like parts.

Referring now to FIG. 1, an embodiment of a supercapacitor as described herein comprises two electrodes, a biocathode 130 and a bioanode 150. These bioelectrodes are separated from each other by a barrier 140. The barrier 140 may be fabricated from an electrically inert material or it may be a separator as described herein. The electrodes and barrier 140 are placed within a capsule 170. The capsule 170 will eventually be filled with electrolyte fluid 180. A bioanode chamber is defined by the walls of the capsule 170 which surround the bioanode 150 and by the surface of the barrier 140 that faces the bioanode 150. A biocathode chamber is defined by the walls of the capsule 170 which surround the biocathode 130 and by the surface of the barrier 140 that faces the bioanode 130. The biocathode 130, the barrier 140, and the bioanode 150 are compressed together by two electrically inert plates 120a and 120b, one positioned parallel to each of the electrodes. The plates 120a and 120b are adjacent to the side of each electrode that is opposite the side facing barrier 140. Two housing walls 110a and 110b are positioned parallel to each of the plates 120a and 120b. These may be constructed of aluminum, carbon fiber, steel, or other material that one of skill in the art would understand to be applicable. In this embodiment, a spring 160 is positioned between the plate 120a that is adjacent to the bioanode 150 and the housing wall 110b. The spring 160 is employed to apply pressure to the electrodes thus keeping them in position. Prior to use, the capsule 170, including the bioanode chamber and the biocathode chamber, will be filled with electrolyte solution 180.

Figure 2:
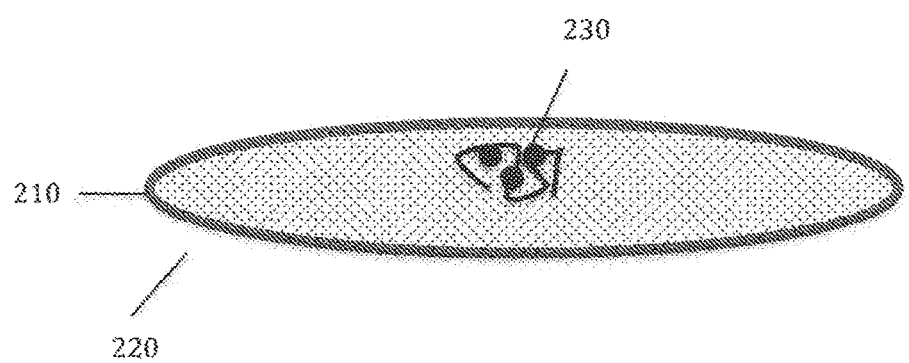
FIG. 2 depicts a schematic diagram of a bioelectrode of the instant disclosure.

Referring now to FIG. 2, the bioelectrode 210 of FIG. 2 may comprise a metal electrode, such as steel or aluminum, and carbon nanotube layer 220 that is well dispersed in a redox-polymer-enzyme 230 matrix. Enzymes of a bioelectrode catalyze redox reactions. It will be appreciated by those skilled in the art that the bioelectrode may also be fabricated with the enzymes covalently bonded to the matrix, or attached with an immobilizer, such as a linker protein, in which case some enzymes may require a mediator in the electrolyte fuel fluid to transfer the charge to the electrode.

Figure 3:
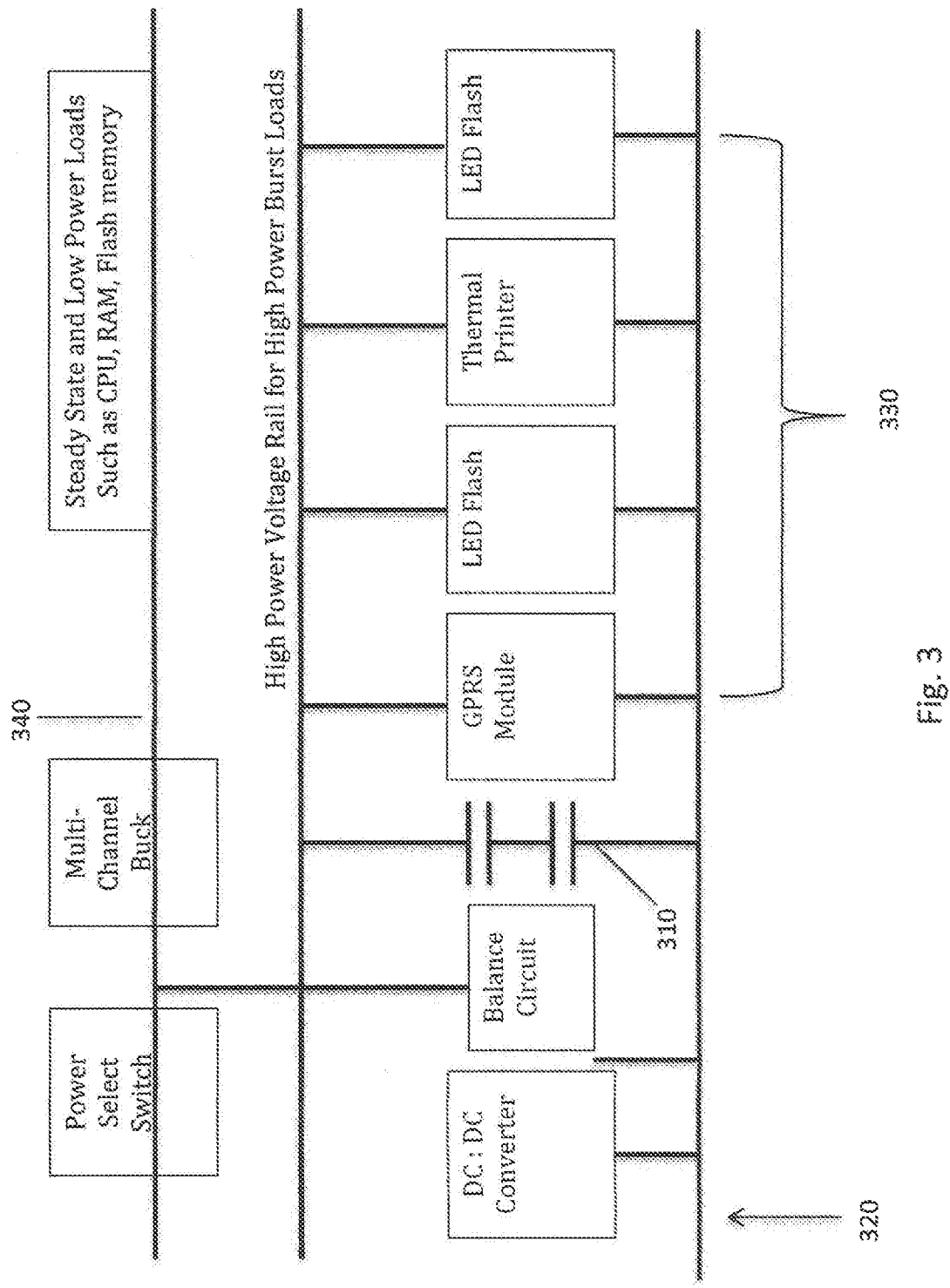
FIG. 3 depicts a schematic view of the biosupercapacitor of the instant disclosure in an electric circuit.

Referring now to FIG. 3, a schematic diagram of a biosupercapacitor 310 of the instant disclosure is positioned in a circuit 320, which provides peak power for all functions of the high power voltage rail 330 and steady state low power voltage rail 340, and backup power for the unit. The biosupercapacitor will provide power in bursts as needed by the different functions on the high voltage power rail 330, and is re-charged in between peaks.

Myriad techniques for immobilizing mitochondria, enzymes, and enzyme cascades exist and may include crosslinking of mitochondria to a carbon electrode in the presence of stabilizing proteins, and/or crosslinking the enzymes to each other for greater efficiency. In some embodiments, the immobilization technique employs non-covalent (van der Waals, hydrophobic-hydrophobic, and ionic) or covalent interactions between unmodified and modified nanotubes. Other embodiments include techniques that employ the adsorption or desorption of intercalation metal oxides or conductive redox polymers. Furthermore, in some embodiments the enzymes to be immobilized are genetically engineered to include artificially added residues or complexes that comprise metal binding sites. These metal binding sites may be allocated to a specific region of on the enzyme, which enables covalent bonding to occur between the enzymes and the immobilization material on the electrode.

More specifically, the immobilizer may be produced from a naturally, or non-naturally occurring, colloidal material, a micellar or inverted micellar material, polymer, membrane, gel, carbon black, carbon nanotubes, and/or graphene. Furthermore, carbon black, nanotubes, and graphene, may be modified, such as with a manganese dioxide coating or other coatings that act as a catalyst for oxygen reduction reaction and may be either single walled (SWCNTs) or multiwalled (MWCNTs).

Referring again to FIG. 1, the bioelectrodes of the instant disclosure comprise a biocathode 130 and a bioanode 150. As discussed above, these bioelectrodes are separated from each other by a barrier 140. The barrier defines the interface between a bioanode chamber and a biocathode chamber. In some embodiments, the barrier 140 may comprise a separator. The separator, as defined herein, comprises a material that absorbs or adsorbs electrolyte 180. Such an electrolyte-absorbing or -adsorbing separator may fill the entire volume between the electrodes. It may be comprised of a membrane, a microporous material, or an ion-conducting material. Exemplary materials for constructing a separator include paper, microporous hydrophilic plastic films, and glass felts. The separator may further comprise an ion-conducting solid, gel, or other material.

Myriad materials, such as collector grids, expanded metal, meshes and foils, or scintered matrixes may be employed in the electrode assembly. It will further be appreciated that biological supercapacitors may be constructed without separators, for instance with a physical separation between electrodes or electrolyte.

The electrolyte 180, as shown in the embodiment of FIG. 1, may be comprised of organic fuels, such as pyruvate or its metabolites (such as succinate, malate, fumarate, acetyl-CoA, citrate, isocitrate, and ketoglutarate), fatty acids and their metabolites, or amino acids.

For electron transfer, the electron may be transferred directly to the electrode, or a mediator may be included in the design. In one aspect of the invention, mitochondria, which also contain the electron transport chain, will allow for the transport of electrons generated from oxidation of the fuel in the Kreb's cycle to the outer surface of the mitochondria for communication with the electrode.

In some embodiments, mediators may be used to conduct or enhance the enzymatic reaction. Appropriate mediators will have good redox potential, reversibility, and other features that increase the lifetime and stability of the device. A common polymeric redox mediator is poly(methylene green) and ferricyanide is a common small molecule mediator. In addition, osmium redox hydrogels, metallacarboranes, and ferrocene-based redox polymers may also be used as mediators. In some embodiments, the mediator comprises a biological enzyme co-factor.

Further, the inclusion of a mediator in a biological supercapacitor in connection with the double layer capacitance phenomenon, may cause charge transfer (Faradaic) to occur between the electrode/electrolyte interface. This is termed pseudocapacitance. Pseudocapacitance is accompanied by an electron charge-transfer between electrolyte and electrode coming from a de-solvated and adsorbed ion.

Biological supercapacitors according to the instant disclosure have a variety of uses. They may be used to provide pulse power, drop test and hot swap support, support for "last gasp" transmissions and "graceful shutdown". In addition, they may be used to enable smaller, cheaper, lighter, and more efficient batteries/power supplies by providing peak power for all functions and backup power for the unit. The battery will only need to deliver average power and the biological supercapacitor will deliver peak power in bursts as needed by the different functions, and is re-charged in between peaks. This also means the DC:DC converter only needs to be sized for average power rather than peak power. Typically the battery would be a Li-ion cell.

Biocompatible and "micro" energy sources are critical to the development of novel commercial bioelectronics, such as health monitoring devices and medical technologies (rapid analysis of DNA, RNA, metabolites—i.e. biomolecule to biosensors), disease treatment devices (nanoscale delivery vehicles that require biocompatibility to interface with tissues or single cells) and neural and biochemical prosthetics (artificial sensory organs that require tissue integration or wireless networks). Additional uses are for self-powered sensors, and bioelectrocatalytic logic gates, consumer and hand-held electronics, the "Internet of Things", smart grid infrastructure, other types of energy generating infrastructure (i.e. wind turbines).

Example 1

Biosupercapacitor Fabrication

In general, the biological supercapacitor according to the instant disclosure comprises a biocathode, a bioanode, a barrier which may comprise a separator positioned between the biocathode and the bioanode, and an electrolytic fuel fluid. Both of the electrodes may comprise a carbon element, for example metallic, glassy carbon or other conventional electrode surfaces onto which one or more enzymes may be immobilized.

In one embodiment, the bioelectrodes comprise buckypaper of various thicknesses (15-250 µm), purity of ~100% MWNTs, and/or CMN grade-buckypaper of 15-250 µm. The carbon nanotube layer can be well dispersed in a redox-polymer-enzyme matrix, for mediated charge transfer. Enzymes of a bioelectrode catalyze redox reactions. It will be appreciated by those skilled in the art that the bioelectrode may also be fabricated with the enzymes covalently bonded to the matrix, or attached with an immobilizer, like a linker protein, in which case they may require mediators in the electrolyte fuel fluid to transfer the charge. Other embodiments may comprise multi-layers of modified Nafion® NRE-212 PEM, bonded redox enzymes, and mediators like poly(methylene green). It will be appreciated by those skilled in the art that the bioelectrode material may also be fastened to a metal disk or plate, such as steel, aluminum, copper, or other metal. A separator is positioned between the biocathode and the bioanode. In separating the bioanode from the biocathode, two chambers are defined.

The biological supercapacitor may further comprise an electrically conductive current collector element immobilized with a biological electron donor or acceptor. In some embodiments, the electrically conductive current collector element may comprise of nickel, copper, aluminum, titanium, or combinations thereof. The current collector element may be connected to elements in a circuit, such as: comparator with hysteresis, microgenerators, active balance circuit, boost converter, single or paired (p-channel) metal-oxide-semiconductor field-effect transistors, and the like.

In one embodiment, the biosupercapacitor may be fabricated by packing and pressing both the bioanode and the biocathode into their respective chambers within a biosupercapacitor cell as is known in the art. Specifically, the cell may resemble a box or container of any shape that will serve to enclose the fuel, the bioanode, and the biocathode, along with a barrier or separator. In one embodiment, the cell comprises PVC. Hardware, including but not limited to bolts and nuts, may be employed to compress the chambers and hold the parts of the apparatus together as described herein as well as ensure that proper seal forms between the biocathode and bioanode chambers. Fuel may then be added to both the bioanode chamber and the biocathode chamber.

In one embodiment, the electrically conductive current collector element is a nickel mesh. This nickel mesh may be connected to the each of the chambers to serve as the current collector and then subsequently connected to a galvanostat for electrochemical characterization. The potentiostat/galvanostat may be interfaced with a computer for data collection of power density, current density and open circuit potential, as well as the charging and discharging profile output generated by the biosupercapacitor. When the biosupercapacitor is in use to power an electrical device, the electrically conductive current collector element may be connected to key circuit features that will interface an energy harvesting source from the biosupercapacitor to the circuit. These include: maximum power tracking, maintaining the output voltage or current of the energy harvesting source so it delivers the maximum possible power, over-voltage protection to ensure the supercapacitor rated voltage is not exceeded, and active balancing to maintain the supercapacitor cells at the same voltage with a low current circuit.

Bioanode Fabrication

In one embodiment, fabrication of the bioanode may be achieved by immobilizing lactate oxidase (LOx) on a laser cut buckypaper anode by mixing the enzymes with C8-LPEI (linear polyethylenimine) hydrogel and cross-linker. To prepare electrodes, 1.125 U of LOx (0.3 mg) may be combined with 154 µl of 10 mg/ml C8-LPEI (in deionized water) and mixed thoroughly. Then 8 µl of a 20% v/v solution of EGDGE (ethylene glycol diglycidyl ether) in deionized water may be added and the solution will again be mixed. Finally, 50 µl of the resulting solution may pipetted onto each electrode and allowed to dry for at least one hour. It will be appreciated by those skilled in the art that the bioanode materials may also be further fastened to a metal disk or plate, such as steel, aluminum, copper, or other metal.

Biocathode Fabrication

In one embodiment, fabrication of the biocathode may be achieved by placing laser-cut buckypaper in a 0.4 mM 1-pyrenemethyl anthracene-2-carboxylate (436 g/mol) solution in methylene chloride for 24 hours. During this time, the pyrene binds to the multi-walled carbon nanotubes (MW-CNTs) within the buckypaper through π-π stacking, leaving the anthracene end free to bind to the bilirubin oxidase (BOD) or laccase (LAC) enzyme, thus orienting the enzyme for better direct electron transfer. The modified buckypaper will be removed from the solution and air-dried, and the leads will be dipped in wax for insulation. Then BOD/LAC will be cast onto the electrode in a TBAB-modified Nafion/PBS solution, which may be synthesized as previously described in the art. Specifically, for electrodes, 1.5 mg of BOD may be mixed thoroughly with 75 µl of 150 mM PBS (130 mM NaCl, 10 mM sodium phosphate monobasic, 10 mM sodium phosphate dibasic, pH-adjusted to 7.4). Next, 25 µl of TBAB-modified Nafion may be added and the solution will be mixed again. Finally, 30 µl of solution may be pipetted onto each cathode and allowed to air-dry for at least an hour. It will be appreciated by those skilled in the art that the biocathode material may also be further fastened to a metal disk or plate, such as steel, aluminum, copper, or other metal.

Fuel

A variety of biomolecules may be used as fuel. The biomolecules typically comprise organic molecules. Examples include, but are not limited to, sugars (including, but not limited to, sucrose, glucose, and fructose), alcohols (including, but not limited to, methanol, ethanol, and glycerol), acids (including, but not limited to, pyruvate and lactate), and fatty acids. In one embodiment, the fuel comprises 200 mM glucose in $O_2$ saturated phosphate buffer, pH 6.4.

High energy density is a very important characteristic of the fuel to be used in the biosupercapacitor. However, the usable energy density is usually decreased significantly when the degree of catalytic oxidation of the fuel is considered, as well as the maximum allowable fuel concentration for the fuel cell. Here, we ensure deep oxidation of fuel by using several enzymes that oxidize the fuel in a stepwise fashion.

EQUIVALENTS

The foregoing written specification is sufficient to enable one skilled in the art to practice the invention. Indeed, various modifications of the above-described means for carrying out the invention, which are obvious to those skilled in the field of biochemistry, molecular biology, electrical engineering, mechanical engineering, or materials science or related fields are intended to be within the scope of the following claims. Although the invention has been shown and described with respect to a certain preferred embodiment or embodiments, it is obvious that equivalent alterations and modifications will occur to others skilled in the art upon the reading and understanding of this specification and the annexed drawings. In particular regarding the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of other embodiments, as may be desired and advantageous for any given or particular application.

We claim:

1. A biological supercapacitor comprising:
a positive electrode, said positive electrode comprising a carbon element, and a first electrically conductive current collector element onto which a first biological electron donor or acceptor is immobilized,
a negative electrode, said negative electrode comprising a carbon element, and a second electrically conductive current collector element onto which a second biological electron donor or acceptor is immobilized, wherein a reaction rate of the first biological electron donor or acceptor and of the second biological electron donor or acceptor are regulated using at least one uncoupler, and wherein said at least one uncoupler is independently selected from the following: rotenone, amytal, antimycin A, cyanide, carbon monoxide, azide, 2,4-dinitrophenol, pentachlorophenol, or oligomycin,
a barrier positioned between the positive electrode and the negative electrode thus separating a bioanode chamber from a biocathode chamber, and
an electrolytic fuel fluid, wherein said electrolytic fuel fluid fills both the bioanode chamber and the biocathode chamber.

* * * * *